United States Patent [19]

Sears

[11] Patent Number: 4,514,960

[45] Date of Patent: May 7, 1985

[54] IN-PACKAGE INSECTICIDAL BAIT PREPARATION UTILIZING MICROWAVE ENERGY

[75] Inventor: Karl Sears, Kendall Park, N.J.

[73] Assignee: American Cyanamid Company, Stamford, Conn.

[21] Appl. No.: 399,030

[22] Filed: Jul. 16, 1982

[51] Int. Cl.³ .............................................. B65B 63/08
[52] U.S. Cl. ....................................... 53/440; 53/127; 424/84; 514/183; 43/131
[58] Field of Search ................. 53/428, 440, 431, 127; 426/1, 401, 243; 43/131; 424/84, 200, 244, 251

[56] References Cited

U.S. PATENT DOCUMENTS

| 4,049,460 | 9/1977 | Broadbent | 424/84 X |
|---|---|---|---|
| 4,087,525 | 5/1978 | Lovell | 424/273 R X |
| 4,163,102 | 7/1979 | Lovell | 424/251 X |
| 4,393,088 | 7/1983 | Matsusaka | 53/440 X |

Primary Examiner—John Sipos
Assistant Examiner—Donald R. Studebaker
Attorney, Agent, or Firm—William H. Calnan

[57] ABSTRACT

A method of preparing a cohesive, solid insecticidal bait within a dispensing package for the bait comprises mixing the bait ingredients, inserting the mixture into the dispensing package, subjecting the mixture-containing package to microwave energy, and cooling.

5 Claims, No Drawings

IN-PACKAGE INSECTICIDAL BAIT PREPARATION UTILIZING MICROWAVE ENERGY

The present invention relates generally to the preparation of cohesive solid insecticidal bait compositions. More particularly, it relates to the preparation of such compositions within a dispensing package with the use of microwave energy.

As the control of household insects has become of greater concern in the country, new methods of control have Exemplary insecticidal bait compositions include those which are disclosed in U.S. application Ser. No. 251,685, filed Apr. 6, 1981, now abandoned the disclosure of which is hereby incorporated by reference, and in U.S. Pat. No. 4,049,460. Suitable dispensing packages for these insecticidal bait compositions include, for example, those disclosed in U.S. application Ser. Nos. 251,672; 251,684 and 251,686, all filed on Apr. 6, 1981 and all now abandoned.

It is an object of the present invention to provide an in-package method of cohesive solid insecticidal bait preparation, thereby providing a simple and inexpensive overall (i.e., the dispensing package containing the insecticidal bait composition) assembly process.

It is a further object of the invention to provide such a method which eliminates problems attendant to the handling of the insecticidal bait after processing, such as contamination of, and/or damage to the bait.

It is an advantage of the instant invention that all of the ingredients for the insecticidal bait composition may be handled cold, i.e., at about room temperature.

These and other objects and advantages are accomplished in accordance with the present invention wherein the various ingredients of the insecticidal bait composition are mixed together at or about room temperature, the paste-like mixture is inserted into a desired package, which package functions as the dispensing means for the bait, the package is subjected to microwave energy whereby the mixture is "melted", and finally the bait-containing package is cooled, yielding a cohesive solid insecticidal bait composition within a dispensing package.

The source of the microwave energy may be any of those systems used in the art. Although simple microwave ovens may be employed, they would not be preferred inasmuch as a batch-type preparation procedure would necessarily be created. A preferred system is one in which the microwave action is part of a continuous process for preparing the final insecticidal bait-containing dispensing package, and it is believed to be within the ordinary skill of one in the art to adapt microwave systems to this end. The type of applicator used to transmit the microwaves is not critical and does not constitute a feature of the present invention.

In accordance with the process of the present invention, the various ingredients which are mixed together at or about room temperature (although the ingredients may be mixed at a somewhat higher or lower temperature, no advantage is seen in so doing), comprises an insecticidal compound, a food attractant (or a mixture of food attractants) which will lure the insect to the dispensing package, and a binder material which upon subjection of the composition to the microwave energy will melt and which upon subsequent cooling will gel the overall composition into a cohesive, solid mass. At least one of the ingredients within the composition must be "microwave-responsive", i.e., it must be affected by the microwaves in such a way as to generate heat within the composition, thereby causing the binder material to melt. Although many binder materials would themselves be microwave responsive, and these are preferably used in the composition it is not necessary that the binder material be microwave-responsive, provided some other component of the composition is microwave-responsive. It is, accordingly, important that the ingredients be thoroughly mixed so that there is intimate contact between those which are microwave-responsive and those which are not. Various commercially available blenders, such as PK Blender are suitable to mix the ingredients.

It is an important aspect of the process of the present invention that the bait mixture not be subjected to the microwave action for too long (or too short) a period of time. Obviously, the mixture must be exposed to the microwave energy for a time sufficiently long to result in satisfactory melting of the binder material so that, upon cooling there will result a cohesive solid composition having the insecticide substantially uniformly distributed therethrough, it being understood, however, that such distribution will also be a function of the mixing of the various ingredients prior to subjection to the microwave energy. However, the composition should not be exposed to the microwave energy for too long a period of time inasmuch as certain components of the composition (such as, but not necessarily exclusively, the insecticide) may degrade or lose functionality upon overexposure. Also, exposure for too long a time may cause the bait mixture to flow out of the area in the dispensing package where the bait is preferably located, although this potential problem may be minimized by appropriately designing the dispensing package such that the bait mixture would remain in the area of initial placement, such as, for example, by molding either a depression into the base of the dispensing package or retaining walls around the placement area. Overexposure may also result in a burning of the bait, making it less attrative to the insects. Extended microwave exposure of the package may further result in deformation or other undesirable effects upon it. Finally, it is a wasteful use of time and money to subject the bait composition to the microwave action for a longer period of time than is minimally required. It has been found, for example, that microwave exposure for about ten (10) seconds is satisfactory when the binder material (which is microwave-responsive) is the polyethylene glycol CARBOWAX TM 8000. However, it will be obvious to those skilled in the art that, depending, inter alia, upon the specific ingredients in the bait composition and the materials of construction of the dispensing package, the optimum microwave exposure time may vary widely, but may easily be determined by routine experimentation.

Any insecticide which will maintain its activity after proceding through the steps of the process of the present invention may be used. Exemplary of such insecticides are organophosphates such as 0,0-diethyl 0-(3,5,6-trichloro-2pyridyl) phosphorothioate and 0,0-diethyl 0-(2-isopropyl-4-methyl-6-pyrimidinyl) phosphorothioate, carbamates such as 2-(1-methylethoxy) phenol methylcarbamate, and inorganic insecticides such as boric acid.

However, in view of the fact that these bait systems will find wide usage in homes and the like, it is preferred that the insecticide not be overly hazardous to humans.

Accordingly, an insecticide such as 1,5-bis(α,α,α-trifluoro-p-tolyl)-1,4-pentadien-3-one(1,4,5,6-tetrahydro-2-pyrimidinyl)hydrazone, the active ingredient in AMDRO® which is made by American Cyanamid Company, is preferred. This insecticide is further preferred due to the fact that it is non-repellent to insects, thereby rendering it even more desirable for use in a bait composition.

The food attractant used may be any one of those foodstuffs which would be eaten by the particular insect sought to be controlled. As is well-known to those skilled in the art, different insects prefer certain foods, and it is not a feature of the present invention to select a specific food attractant for a given targeted insect. However, it is to be noted that, unless some other component of the bait composition is solid material which will function as a "base" for the composition, then the food attractant, or one of the food attractants if more than one is used, must be a solid. Exemplary solid foods include oatmeal, dog food, flour and potatoe flakes. Liquid foods include honey, molasses, maply syrup, corn syrup and soybean oil.

As for the binder material, any material which may be mixed with the remaining ingredients of the bait and which will melt upon subjection of the composition to the microwave energy and solidify upon subsequent cooling may be utilized. It is preferred that the binder not be repellant to the target insect. Suitable binders include waxes, such as a paraffin, ceresin wax, candillilla wax, POLAWAX™, beeswax, carnauba wax, microcrystalline waxes and polyethylene waxes. Preferably, as stated above, the binder material itself is microwave-responsive.

It is to be noted that other materials, such as preservatives, colorings, and the like may also be incorporated into the insecticidal bait composition. It may also be necessary in some instances to render the insecticide more dispersible in the bait composition, and accordingly, materials to accomplish this purpose may also be present in the composition.

Although it is not a particular feature of, or limitation on, the process of the present invention, the insecticide typically comprises about 0.25 to 5%, preferably 0.5 to 3%, by weight, of the bait composition. The food attractant(s) will generally comprise the major portion of the composition—typically up to about 80%, by weight, thereof, with the binder material comprising the remainder thereof—typically from about 5 to 20%, by weight. However, in certain instances, depending, inter alia, upon the nature of the various ingredients, the binder material may comprise more of the overall composition than the food attractant(s).

The dispensing package chosen for use in the process of the present invention is not critical. It is important only that the package be substantially resistant to degradation during, or as a result of, the microwave treatment, and this will be a function of, inter alia, the material out of which the package is constructed, as well as the binding material (glue, etc.), if any, used to seal various parts of the package together and the amount of microwave exposure needed to satisfactorily treat the insecticidal bait composition. It is believed to be well within the skill of one possessing ordinary skill in the art to select a suitable material of construction for the dispensing package. For example, various plastics, such as polypropylene, are known to be safe for use in microwave ovens and the like, and, for economic reasons, these plastics, particularly polypropylene, are preferred.

The particular design of the dispensing package is also not a feature of the present invention. However, it is necessary that the package have a location therein whereinto the paste-like mixture of insecticide, food attractant and binder may be put, ultimately (following completion of the process of the present invention) to be a cohesive solid mass "attached" to the package. By "attached" is meant that the insecticidal bait mixture, upon melting and subsequent cooling, forms some degree of bonding with the package, through adhesion of the like. Particularly preferred dispensing packages for use in the process of the present invention include those disclosed in commonly assigned, copending applications Ser. No. 251,672; 251,684 and 251,686, all filed on Apr. 6, 1981, the disclosures of which are hereby incorporated by reference.

The invention will now be illustrated by the following non-limitative examples. In the examples, all parts and percentages are by weight unless otherwise indicated, and all temperatures are in degrees centigrade.

EXAMPLE 1

An insecticidal bait composition was prepared as follows: 6% isopropanol, 2% AMRDO®, 0.2% DOWICIL™ 200 (Cis isomer of 1-(3-Chloroallyl)-3,5,7-triaza-1-azonia-adamantane chloride, an antimicrobial) and 2% oleic acid were mixed together at room temperature. 11.8% CARBOWAX™ 8000 (a polyethylene glycol, made by Union Carbide Corporation) and 40% corn syrup were separately mixed together at room temperature, and the two separate mixtures were then mixed together in a static mixer. Into this mixture was then blended 38% oatmeal, using a Ribbon blender, to a total of 100%. The composition was paste-like in nature.

About 8 grams of this composition were placed in the central area of three (3) of the dispensing packages disclosed in U.S. Application Ser. No. 251,684, supra. Two of the packages did not have the covers (or lids) affixed, while the third package had its cover affixed by sonic welding.

All three packages were then placed in a Litton Home Microwave Oven for ten (10) seconds, removed and allowed to cool to room temperature. The bait compositions were cohesive solids. Subsequent testing of the bait composition established that the insecticide had not lost efficacy.

What is claimed is:
1. A process for preparing a cohesive solid insecticidal bait composition within a dispensing package therefor which comprises:
   (a) intimately mixing an insecticidal composition, a food attractant, a binder material, and a microwave-responsive material in the event the insecticidal composition, food attractant and binder material are not microwave-responsive, together into a paste-like material at a temperature below the melting point of said binder material;
   (b) inserting said paste-like material into said package;
   (c) treating said paste-like material-containing package with microwave energy for a period of time sufficient to cause said binder material to melt; and
   (d) cooling said package to form a cohesive, solid insecticidal bait composition.
2. The process of claim 1 wherein said binder material is microwave-responsive.

3. The process of claim 1 or claim 2 wherein the insecticidal composition is a pentadienone hydrozone.

4. The process of claim 1 or claim 2 wherein the insecticidal composition is 1,5-bis($\alpha, \alpha, \alpha$-trifluoro-p-tolyl)-1,4-pentadien-3-one 1,4,5,6-tetrahydro-2-pyrimidinyl) hydrazone, the food attractant comprises corn syrup and oatmeal, and the binder is polyethylene glycol.

5. The process of claim 4 wherein the treatment time is about ten seconds.

* * * * *